United States Patent [19]

Hudson

[11] Patent Number: 5,567,738
[45] Date of Patent: Oct. 22, 1996

[54] USE OF 2-(4-(4-CHLORO-PHENYL)CYCLOHEXYL)-3-HYDROXY-1,4-NAPHTHOQUINONE FOR THE TREATMENT OF CANCER

[75] Inventor: Alan T. Hudson, Beckenham, Great Britain

[73] Assignee: Glaxo Wellcome Inc., Research Triangle Park, N.C.

[21] Appl. No.: 379,617

[22] PCT Filed: Aug. 6, 1993

[86] PCT No.: PCT/GB93/01669

§ 371 Date: Jan. 31, 1995

§ 102(e) Date: Jan. 31, 1995

[87] PCT Pub. No.: WO94/03163

PCT Pub. Date: Feb. 17, 1994

[30] Foreign Application Priority Data

Aug. 7, 1992 [GB] United Kingdom ............ 9216859

[51] Int. Cl.$^6$ .................................................. A61K 31/12
[52] U.S. Cl. .................................................. 514/682
[58] Field of Search ........................................ 514/682

[56] References Cited

U.S. PATENT DOCUMENTS

| | | | |
|---|---|---|---|
| 2,533,648 | 5/1951 | Fieser et al. | 260/306 |
| 3,347,742 | 10/1967 | Rogers | 167/53.2 |
| 3,367,830 | 2/1968 | Sarett | 167/53.1 |
| 4,981,874 | 1/1991 | Latter et al. | 514/682 |
| 5,053,418 | 10/1991 | Latter et al. | 514/682 |
| 5,053,432 | 10/1991 | Hudson et al. | 514/682 |
| 5,206,268 | 4/1993 | Latter et al. | 514/548 |
| 5,310,762 | 5/1994 | Latter et al. | 514/682 |

FOREIGN PATENT DOCUMENTS

| | | |
|---|---|---|
| 0002228B1 | 6/1979 | European Pat. Off. . |
| 0077551A2 | 4/1983 | European Pat. Off. . |
| 0077550B1 | 4/1983 | European Pat. Off. . |
| 0123239A2 | 10/1984 | European Pat. Off. . |
| 0123238A2 | 10/1984 | European Pat. Off. ............ 514/682 |
| 0362996A2 | 4/1990 | European Pat. Off. ............ 514/682 |
| 1141735 | 1/1969 | United Kingdom ............ 514/682 |
| 1268316 | 3/1972 | United Kingdom ............ 514/682 |
| 1553424 | 9/1979 | United Kingdom . |

OTHER PUBLICATIONS

Wofsy, pp. 377–401, Chapter 36, 1986.
Fieser, et al., vol. 70, pp. 3156–3165, 1948.
Hughes, Parasitology Today, vol. 3, No. 11, pp. 332–335, 1987.
Discriminant Analysis and Structure–Activity Relationships. 1. Naphthoquinone; J. Med. Chem; vol. 21; No. 4; 1978; pp. 369–374.
Role of the Naphthoquinone Moiety in the Biological Activities of Sakyomicin A: J. Antibiot. vol. 39; No. 4; 1986; pp. 557–563.
Inhibition of Thioredoxin Reductase (E.C. 1.6.4.5.) by Antitumor Quinones; Free Rad. Res. Commun. vol. 8; No. 4–6; 1990; pp. 365–372.

*Primary Examiner*—Jerome D. Goldberg
*Attorney, Agent, or Firm*—George W. Neuner

[57] ABSTRACT

The present invention relates to the use of 2-[4-(4-chlorophenyl)cyclohexyl]-3-hydroxy-1,4-naphthoquinone or a physiologically acceptable salt or other physiologically functional derivative thereof for the manufacture of a medicament for the treatment of tumours in animals, to pharmaceutical compositions for the treatment of tumours in animals, to pharmaceutical compositions for the treatment of tumours, comprising said compound as active ingredient and to a method of treating tumours in an animal which comprises administering to said animal an effective amount of said compound.

6 Claims, No Drawings

USE OF 2-(4-(4-CHLOROPHENYL)CYCLOHEXYL)-3-HYDROXY-1,4-NAPHTHOQUINONE FOR THE TREATMENT OF CANCER

This application is a 371 of PCT/9B93/01669 filed Aug. 6, 1993.

The present invention relates to the treatment of cancer. More particularly, the invention is concerned with the use of 2-[4-(4-chlorophenyl)cyclohexyl]-3-hydroxy-1,4-naphthoquinone and physiologically acceptable salts and physiologically functional derivatives thereof as anti-tumour agents, and the use of said compound for the manufacture of medicaments for the treatment of cancer.

Research in the area of cancer chemotherapy has produced a variety of anti-tumour agents, which have differing degrees of efficacy. Standard clinically used agents include adriamycin, actinomycin D, methotrexate, 5-fluorouracil, cis-platinum, vincristine and vinblastine. However, these presently available anti-tumour agents are known to have various disadvantages, such as toxicity to healthy cells, and common side effects of anti-tumour drugs include alopecia and skin toxicity.

The compound 2-[4-(4-chlorophenyl)cyclohexyl]-3-hydroxy-1,4-naphthoquinone has previously been disclosed, for example in European Patent No. 123,238 which relates to 2-substituted-3-hydroxy-1,4-naphthoquinones of formula (I)

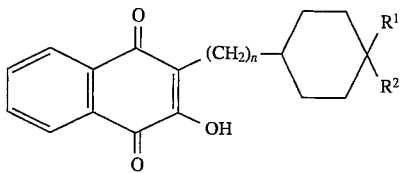

wherein either $R^1$ is hydrogen and $R^2$ is selected from $C_{1-6}$ alkoxy, aralkoxy, $C_{1-6}$ alkyl-$C_{1-6}$ alkoxy, phenyl substituted by one or two groups selected from halogen and $C_{1-6}$ alkyl, halogen and perhalo-$C_{1-6}$ alkyl or $R^1$ and $R^2$ are both $C_{1-6}$ alkyl or phenyl, and n is zero or 1, and physiologically acceptable salts thereof. The compounds are said to have antiprotozoal activity. Specifically, compounds of formula (I) wherein n is zero are said to be active against the human malaria parasite *Plasmodium falciparum* and also against Eimeria species such as *E.tenella* and *E.acervulina,* which are causative organisms of coccidiosis and compounds of formula (I) where n is 1 are said to be active against protozoa of the genus Theileria, in particular *T.annulata* or *T.parva.* Amongst the compounds specifically named and exemplified is the compound of formula (I) wherein n is zero, $R^1$ is hydrogen and $R^2$ is 4-chlorophenyl, i.e. 2-[4-(4-chlorophenyl)cyclohexyl]-3-hydroxy-1,4-naphthoquinone.

It has now surprisingly been found that 2-[4-(4-chlorophenyl)cyclohexyl]-3-hydroxy-1,4-naphthoquinone, represented in this specification by formula (II):

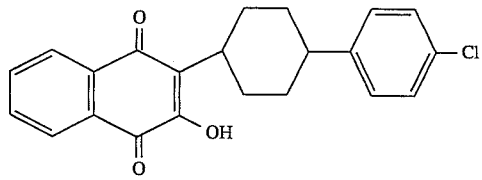

exhibits activity against tumour cells, more specifically against carcinoma, adenocarcinoma and fibrosarcoma cells.

Thus, in a first aspect the present invention provides the use of the compound of formula (II) and physiologically acceptable salts and other physiologically functional derivatives thereof for the manufacture of a medicament for the treatment of tumours in mammals (including humans).

According to a further aspect the present invention provides a method for the treatment of tumours in mammals, including humans which comprises the administration of an effective amount of a compound of formula (II), or a physiologically acceptable salt or other physiologically functional derivative thereof.

Treatment is particularly important for immunocompromised individuals, such as people with AIDS, who are more susceptible to certain types of tumour than people with a normally functioning immune system.

The hydroxyl group in the compound of formula (II) may form salts with appropriate bases, and physiologically acceptable salts of the compound (II) include inorganic base salts such as alkali metal (e.g. sodium and potassium) salts and alkaline earth metal (e.g. calcium salts; organic base salts e.g. phenylethylbenzylamine, dibenzylethylenediamine, ethanolamine and diethanolamine salts; and amino acid salts e.g. lysine and arginine.

Physiologically functional derivatives of formula (II) are derivatives which are converted in vivo to a compound of formula (II). Such derivatives include those described in EPO362996 and EPO537947.

It will be appreciated that the compound of formula (II) may exist as the cis or trans isomer, that is to say that the cyclohexyl ring may be cis or trans substituted by the naphthoquinone nucleus and the chlorophenyl group. Both cis and trans isomers and mixtures thereof in any ratio may be used in accordance with the present invention. In general when the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required; typical mixtures include those in which the cis/trans isomer ratio is about 1:1,40:60 and 5:95. For use according to the present invention the trans isomer of the compound of formula (II), or a mixture of its cis and trans isomers containing at least 95% e.g. 99% of the trans isomer, is preferred.

The compound of formula (II) may also exist in a tautomeric form in which the hydroxyl group donates its proton to one of the oxo groups and the use of such tautomeric forms is included within the scope of this invention. However, it is believed that the stable form is that shown in formula (II).

The amount of compound of formula (II) required to be effective as an anti-tumour agent will, of course, vary and is ultimately at the discretion of the medical or veterinary practitioner. The factors to be considered include the route of administration and nature of the formulation, the mammal's bodyweight, age and general condition and the nature of the tumour to be treated. In general, a suitable effective anti-tumour dose for administration to man is in the range of 1.0 mg to 200 mg per kilogram bodyweight per day, for example from 5 mg/kg to 100 mg/kg, particularly 20 to 100 mg/kg.

It should be understood that the dosages referred to above are calculated in terms of the compound of formula (II) per se.

For use according to the present invention the compound of formula (II) or a physiologically acceptable salt or other physiologically functional derivative thereof is preferably presented as a pharmaceutical formulation.

Pharmaceutical formulations comprise the active ingredient (that is, the compound of formula (II) or a physiologically acceptable salt or other physiologically functional derivative thereof) together with one or more pharmaceutically acceptable carriers thereof and optionally other therapeutic and/or prophylactic ingredients. The carrier(s) must be acceptable in the sense of being compatible with the other ingredients of the formula and not deleterious to the recipient thereof.

The compound of formula (II) or its salt or other physiologically functional derivative may conveniently be presented as a pharmaceutical formulation in unit dosage form. A convenient unit dose formulation contains the active ingredient in an amount of from 10 mg to 3 g, e.g. 50 mg to 3 g. A typical unit dose may contain for example 50 mg, 1 g, 2 g or 3 g of the active ingredient.

Pharmaceutical formulations include those suitable for oral, topical (including dermal, buccal and sublingual), rectal and parenteral (including subcutaneous, intradermal, intramuscular and intravenous), administration as well as administration by naso-gastric tube. The formulation may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredient either alone or in admixture with one or more accessory ingredients, into the capsule shells and then sealing them in the usual manner. Cachets are analogous to capsules wherein the active ingredient together with any accessory ingredient(s) is sealed in a rice paper envelope. The compound of formula (II) or a physiologically acceptable salt or other physiologically functional derivative thereof may also be formulated as dispersible granules, which may for example be suspended in water before administration, or sprinkled on food. The granules may be packaged e.g. in a sachet. Formulations suitable for oral administration wherein the career is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredient is formulated in an appropriate release—controlling matrix, or is coated with a suitable release—controlling film. Such formulations may be particularly convenient for prophylactic use.

The active ingredient my also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compound of formula (II) or a physiologically acceptable salt or other physiologically functional derivative thereof may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The compound of formula (II) or a physiologically acceptable salt or other physiologically functional derivative thereof may also be used in accordance with the present invention in combination or concurrently with other therapeutic agents, for example agents used in the treatment of immunocompromised patients, including antibacterial agents; antifungal agents; anticancer agents such as interferons e.g. alpha-interferon; antiviral agents such as azidothymidine (AZT,zidovudine); immunostimulants and immunodulators. The compound of formula (II) may also be administered in combination with a 4-pyridinol compound, as described in EPA 123,239 e.g. 3,5-dichloro 2,6-dimethylpyridinol(meticlorpindol). The compound of formula (II) may also be administered in combination or concurrently with anti-diarrhoeal agents such as loperamide hydrochloride and/or diphenoxylate hydrochloride, or with morphine sulphate. Oral rehydration therapy may also be carried out concurrently.

Compositions suitable for veterinary use include those adapted for oral, parenteral, and intrarumenal administration.

Compounds suitable for oral administration include drenches (oral liquid dosing), which may be solutions or suspensions; tablets, boluses, pastes, or in-feed preparations in the form of powders, granules or pellets.

Alternatively, veterinary compositions may be adapted to be administered parenterally by sub-cutaneous, intramuscular or intravenous injection of a sterile solution or suspension, by implantation or as an intramammary injection whereby a suspension or solution is introduced into the udder via the teat.

For intrarumenal injection, the compositions of the invention may be solutions or solid or microcapsule suspensions. Typically the compositions are similar to the oral liquid preparations or parenteral preparations described herein.

Such compositions are injected directly into the rumen, usually through the side of the animal, for example by a hypodermic syringe and needle or by an automatic injection device capable of giving single or multiple doses.

For veterinary administration the compound of formula (II) or its salt or other physiologically functional derivative is preferably formulated with one or more veterinarily acceptable carriers.

For oral administration, fine powders or granules may contain diluting agents, for example lactose, calcium carbonate, calcium phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethylcellulose, guar based vegetable gums, sodium alginates or sodium starch glycolates; granulating or binding agents such as starch in the form of mucilage starch derivatives, such as "Snow Flake", cellulose derivatives such as talc, calcium stearate, methyl cellulose, gelatin or polyvinylpyrrolidone; and/or lubricating agents, such as magnesium stearate or stearic acid. For parenteral administration, the compounds may be presented in sterile injection solutions which may contain antioxidants or buffers, or as injectable suspensions. Suitable solvents include water, in the case of suspensions, and organic solvents such as dimethylformamide, dimethylacetamide, diethylacetamide, ethyl lactate, ethyl akate, dimethylsulphoxide, alcohols, e.g. ethanol, glycols, e.g. ethylene glycol, propylene glycol, butylene glycol and hexamethylene glycol, polyethylene glycols containing 2 to 159 ethylene glycol monomer units and having average molecular weights from about 90 to 7500, glycerin formal, glycofural, glycerol, isopropylmyristate N-methylpyrrolidone, 2-pyrrolidone polyethylene glycoethers of tetrahydrofurfuryl alcohol and diethylene glycol, and fixed and neutral oils, for example fractionated coconut oil. Parenteral formulations may also contain isotonic agents.

For veterinary use the compound of formula (II) may be employed together with other therapeutic agents used in the field of animal health, for example with anticoccidial and/or antitheilerial agents.

Methods for preparing the compound of formula (II) are described in EP 123,238, and one specific method is illustrated in Example 1.

EXAMPLE 1

2-[trans-4-(4-Chlorophenyl)cyclohexyl]-3-hydroxy-1,4-naphthoquinone a) 4-(4-Chlorophenyl)cyclohexane-1-carboxylic Acid Acetyl chloride (30 g) and finely powdered aluminium chloride (60 g) were stirred together in carbon disulphide (120 ml) and then cooled to −50° C., in a $CO_2$/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water, dried over anhydrous sodium sulphate and evaporated to dryness. The product was distilled in vacuo, the fraction boiling at 140°–154° C. (0.1 mm Hg) collected, diluted with an equal volume of petroleum ether (40–60), cooled to −6° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl)cyclohex- ane-1-carboxylic acid, m.p. 254°–256° C.

b) 2-[4-(4-chlorophenyl)cyclohexyl]-3-chloro-1,4-naphthoquinone

A mixture of 2-chloro-1,4-naphthoquinone (3.95 g, 0.02 mol), 4-(4-chlorophenyl)cyclohexane-1-carboxylic acid (4.9 g, 0.02 mol) and powdered silver nitrate (1.05 g, 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours then cooled in ice for 30 mins, after which it was filtered, and the residual sticky solid extracted twice with boiling chloroform to remove inorganic material. The chloroform was removed by evaporation to leave a yellow-brown solid (ca 2.7 g). This was dissolved in 40 nl of boiling acetonitrile; a little insoluble material was removed by filtration. On cooling, the title compound separated as yellow crystals, (550 mg) m.p. 172°–175° C.

NMR, $dH(d_6$-DMSO) 8.05(2H, mult., b-naphth), 7.85 (2H, mult., a-naphth), 7.30 (4H, s., PhH), 3.30 (1H, br.t., CH), 2.67 (1H, br.t., CH), 1.2–2.4 (8H, mult., 4×$CH_2$).

c) 2-[4-(4-chlorophenyl)cyclohexyl]-3-hydroxy-1,4-naphthoquinone

The product of stage (b) was suspended in 10 ml of boiling methanol and 0.55 g of potassium hydroxide in 5.5 ml of water was added dropwise over 15 mins. The mixture was refluxed until a dark red solution formed, (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200°–209°, were recrystallised from acetonitrile to give the title product as the trans-isomer (300 mg) m.p. 216°–219° C.

EXAMPLE 2

The following examples illustrate, with reference to the compound of formula (II) per se, pharmaceutical and veterinary formulations which may be employed in accordance with the present invention.

A. Injectable solution

A solution for intramuscular injection may be prepared by mixing:

| | |
|---|---|
| Compound of formula (II) | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

B. Injectable solution

The following injectable formulation was prepared:

| | |
|---|---|
| Compound of formula (II) | 5 parts by weight |
| N-methyl-pyroflidone | 48.3 parts by weight |
| Tween 80 | 2 parts by weight |
| Span 80 | 4.7 parts by weight |
| Miglyol 812 | 40 parts by weight |
| | 100.0 |

C. Tablet

| | |
|---|---|
| Compound of formula (II) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LBPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

D. Oral suspension

| | |
|---|---|
| Compound of formula (II) | 50 mg |
| Avicel RC 591 | 75 mg |
| Sucrose syrup | 3.5 mg |
| Methylhydroxybenzoate | 5 mg |
| Colour | 0.01% w/v |
| Cherry flavour | 0.1% v/v |
| Tween 80 | 0.2% v/v |
| Water | to 5 ml |

E. Injectable suspension

| | |
|---|---|
| Compound of formula (II) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

F. Capsule

| | |
|---|---|
| Compound of formula (II) | 100 mg |
| Starch 1500 | 150 mg |
| Magnesium stearate | 2.5 mg |
| filled into a hard gelatin capsule | |

G. Aqueous Suspension

An aqueous suspension may be prepared as follows:

| | |
|---|---|
| Compound of formula (II) | 1.00 part by weight |
| Neosyl | 16.00 parts by weight |
| Bentonite | 3.20 parts by weight |
| Glycerin | 15.00 parts by weight |
| Sodium benzoate | 1.00 part by weight |
| Bevaloid 35/2 | 1.00 part by weight |
| Thymol | 0.04 parts by weight |
| Water | 62.76 parts by weight |
| | 100.00 |

H. Salt Block

A salt block may be prepared by mixing a finely divided compound of formula (II) (0.5 parts by weight) with sodium chloride (99.5 parts by weight) and the mixture pressed into blocks.

I. Paste

The following paste may be prepared:

| | |
|---|---|
| Compound of formula (II) | 3.0 parts by weight |
| Gum tragacanth | 4.0 parts by weight |
| Bevaloid 35/3 | 1.0 part by weight |
| Nipagin "M" | 0.1 parts by weight |
| Glycerin | 19.0 parts by weight |
| Water | 72.9 parts by weight |
| | 100.00 |

The use of the compound of formula (II) according to the present invention is illustrated by the following example:

BIOLOGICAL TEST RESULTS

EXAMPLE 3

Activity Against Tumour Cell Lines In Vitro

Test Compound

A: 2-[trans-4-(4-chlorophenyl)cyclohexyl]-3-hydroxy-1,4-naphthoquinone

Method

The activity of the test compound was evaluated using proliferative assays against a number of different turnout cell lines in vitro.

The results, which are presented in Table 1 below, indicate that the test compound was active, at 1001 μM concentration, against all the cell lines tested.

TABLE 1

| Cell Line | Concentration (μM) | Activity (% Growth Inhibition) |
|---|---|---|
| P3888D1 (Mouse Leukaemia) | 100 | 92.26 |
| DLD-1 (Human colon adenocarcinoma) | 100 | 94.18 |
| WiDr (Human colon adenocarcinoma) | 100 | 79.44 |
| HCT-116 (Human colon carcinoma) | 100 | 93.75 |
| A549 (Human lung carcinoma) | 100 | 86.57 |

EXAMPLE 4

Activity Against Human Fibrosarcoma Cells In Vitro

Test Compound

A: 2-[trans-4-(4-chlorophenyl)cyclohexyl]-3-hydroxy-1,4-naphthoquinone

Method

The activities of the test compound and of a soluble carbamate derivative thereof against two cell lines derived from human fibrosarcoma cells were measured.

The results, which are presented in Table 2 below, show that both the compound and the soluble derivative were active. The higher activity of the soluble derivative was almost certainly due to increased ease of formulation of the soluble derivative compared with the test compound per se.

TABLE 2

| | $IC_{50}$ (µM) | |
|---|---|---|
| | HT1080SCC2 | HT10801C |
| Test Compound | 11 | 15 |
| Soluble Derivative | 5.3 | 7.0 |

I claim:

1. A method of treating a mammal having a carcinoma tumour which comprises administering to said mammal an effective carcinoma tumour treatment amount of 2-[4-(4-chlorophenyl)cyclohexyl]- 3-hydroxy-1,4-naphthoquinine in the form of its trans isomer or a mixture of its cis and trans isomers containing at least 95% of the trans isomer or a physiologically acceptable salt thereof.

2. The method of claim 1 wherein the amount administered is 20 to 100 mg/kg of mammal bodyweight per day.

3. A method of treating a mammal having an adenocarcinoma tumour which comprises administering to said mammal an effective adenocarcinoma tumour treatment amount of 2-[4-(4-chlorophenyl)cyclohexyl]-3-hydroxy-1,4-naphthoquinine in the form of its trans isomer or a mixture of its cis and trans isomers containing at least 95% of the trans isomer or a physiologically acceptable salt thereof.

4. The method of claim 3 wherein the amount administered is 20 mg to 100 mg/kg of mammal bodyweight per day.

5. A method of treating a mammal having a fibrosarcoma tumour which comprises administering to said mammal an effective fibrosarcoma tumour treatment amount of 2-[4-(4-chlorophenyl)cyclohexyl]-3-hydroxy-1,4,-naphthoquinine in the form of its trans isomer or a mixture of its cis and trans isomers containing at least 95% of the trans isomer or a physiologically acceptable salt thereof.

6. The method of claim 5 wherein the administered is 20 to 100 mg/kg of mammal bodyweight per day.

* * * * *